United States Patent [19]

Bromberg et al.

[11] Patent Number: 4,600,494
[45] Date of Patent: Jul. 15, 1986

[54] ION ANALYZER CALIBRATION CELL

[75] Inventors: Edward E. A. Bromberg, Peabody; Albert Diggens, Weston; Steven J. West, Hull; James W. Ross, Cambridge, all of Mass.

[73] Assignee: Orion Research, Inc., Cambridge, Mass.

[21] Appl. No.: 647,313

[22] Filed: Sep. 4, 1984

[51] Int. Cl.⁴ .......................................... G01N 27/28
[52] U.S. Cl. ................................ 204/401; 73/1 R; 422/102
[58] Field of Search ............... 422/102; 204/401, 400, 204/416, 417, 418, 419, 420, 435, 1 T; 73/1 R; 324/425, 438

[56] References Cited

U.S. PATENT DOCUMENTS

| | | | |
|---|---|---|---|
| 3,705,018 | 12/1972 | Taylor | 422/102 X |
| 3,725,236 | 4/1973 | Johnson | 204/400 X |
| 3,770,608 | 11/1973 | Kelch et al. | 204/416 X |
| 3,881,997 | 5/1975 | Johnson et al. | 204/1 T |

OTHER PUBLICATIONS

E. Pungor et al., "Ion-Selective Electrodes", pp. 175-198, (1978).

*Primary Examiner*—G. L. Kaplan
*Attorney, Agent, or Firm*—Cesari and McKenna

[57] ABSTRACT

Apparatus for calibrating an ion analyzer comprises a calibration cell having defined therein a first volume for measuring an ion concentration of a sample when the instrument is operated in a monitoring and a second volume for measuring the ion concentration when the instrument is operated in a calibration mode. The first volume is included in, and forms part of, the second volume so that the matrix for the calibration measurement is essentially identical to that for the sample measurement. A double known-addition is used during the calibration mode to determine the calibration parameters.

8 Claims, 3 Drawing Figures

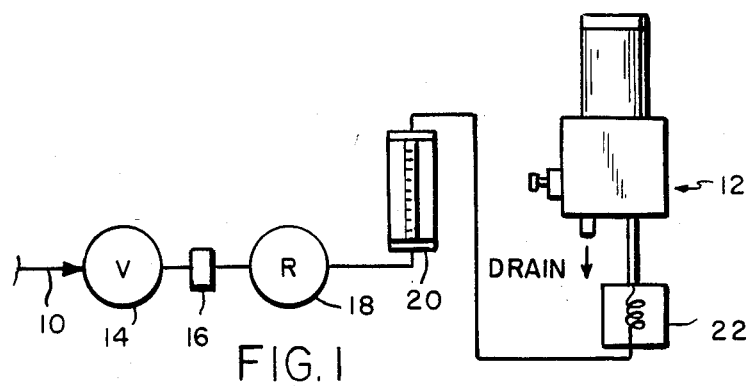
FIG. 1
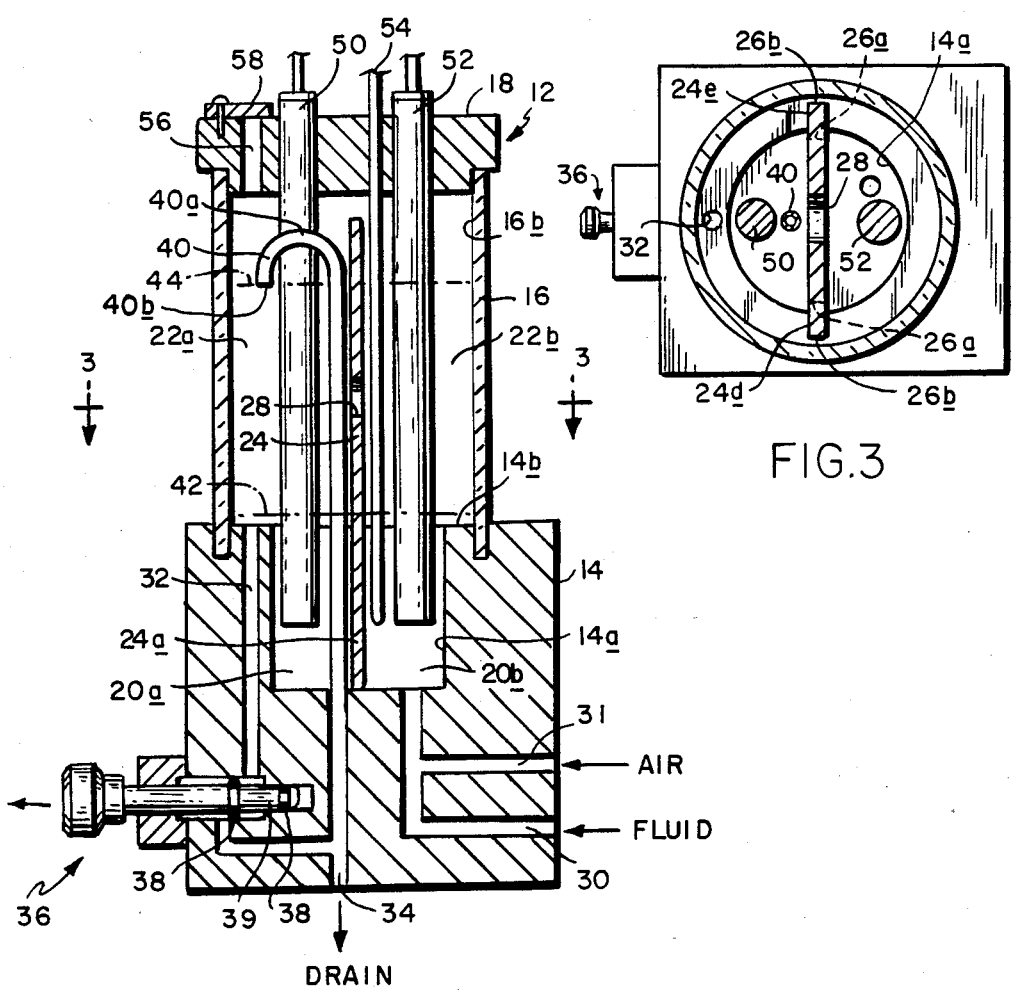
FIG. 2
FIG. 3

ION ANALYZER CALIBRATION CELL

BACKGROUND OF THE INVENTION

1. Field of the Invention

The invention relates to ion analyzers and, specifically to ion analyzers using potentiometric measuring techniques; it comprises a method and apparatus for rapidly and accurately calibrating the analyzer.

2. Prior Art

Ion analyzers measure the concentration of ions in solution. Potentiometric ion analyzers have found widespread use because they enable rapid and accurate measurements by relatively inexperienced personnel without elaborate wet-chemistry techniques. These analyzers have found extensive use in both laboratory and industrial settings.

In order to insure continued accuracy, it is necessary to re-calibrate the analyzers periodically. In the case of potentiometric analyzers, this involves determining the reference potential, $E_O$, and the slope, b, which are defined by the well-known Nernst equation ($E = E_O - b \log C$). Various techniques have been proposed to perform this calibration, but none are wholly satisfactory.

SUMMARY OF THE INVENTION

In accordance with the present invention, a measuring and calibration cell has a liquid-containment chamber which is used for both sample measurement and instrument calibration. Ion-sensitive electrodes extend into the liquid sample in the cell and provide a voltage output which is indicative of the concentration of the ion of interest in the solution. Measurements are made in two different modes, namely, the monitor mode and the calibration mode. In the monitor mode, measurements are made on the sample without the addition of further materials thereto. In the calibration mode, in contrast, measurements are made on a sample in both a diluted and an undiluted form.

In particular, in the calibration mode, the sample is first measured in its undiluted form. Next, it is diluted with a small aliquot of a solution containing a known concentration of the ion whose concentration in the sample solution is to be measured. Air is bubbled through the solution to thoroughly mix the additive and the sample. A measurement is then made on the sample solution as so diluted. The dilution is next repeated with a solution of even greater concentration in the ion whose concentration in the sample solution is to be measured, and a final measurement made. These three measurements enable determination of the three unknowns in the Nernst equation, that is the reference potential $E_O$, the slope b, and the concentration C. The quantities $E_O$ and b are the desired calibration parameters.

In the preferred embodiment of the invention, the measuring and calibration cell defines a first volume for measuring the concentration during the monitor mode, and defines a second, larger volume for measurements during the calibration mode. In one model of instrument built in accordance with the present invention for the purpose of measuring sodium ion concentration in the boiler water of electric power generating plants, the liquid-containment cell was chosen to define a volume of 20 milliliters during the sample-measurement mode and a volume of approximately 100 milliliters (more precisely 95 milliliters) in the calibration mode. The small sampling volume allows rapid response of the instrument during normal sample measurements. For example, at a flow rate of 20 milliliters per minute the sample volume is cleared in approximately 1 minute. At the same time, the larger volume utilized for the calibration mode enhances the accuracy of the calibration.

The two volumes are formed within the same cell and, indeed, the smaller volume forms part of the larger volume. This insures that the environment for monitoring purposes is the same as the environment for calibration purposes. Thus, the sample-measurement and calibration are performed on the same "matrix" of constituents, and calibrations errors are thereby minimized.

The electric potential measurements, which are indicative of the concentration of the ion in solution, are performed by a pair of electrodes extending into the calibration cell. A first electrode serves as the measuring electrode, while a second electrode serves as a reference electrode. Typically, the reference electrode comprises an electrode of the type having a porous frit through which an internal electrolyte solution slowly flows in order to form a conductive path between an inner electrode and the sample solution. A baffle plate interposed between the reference electrode and the measuring electrode isolates the former from the turbulence generated by the mixing bubbles and thereby enhances the electrical response of the reference electrode. The baffle effectively divides the liquid-containment cell into two separate portions. However, it does not totally isolate them from each other and, indeed, means are provided to insure continuous liquid communication between the two sections of the cell in order to insure that both the reference and the measuring electrodes are exposed to the same sample solution.

DETAILED DESCRIPTION OF THE PREFERRED INVENTION

The foregoing and other and further objects and features of the invention will be more readily understood on reference to the following detailed description of the invention, when taken in conjunction with the accompanying drawings, in which:

FIG. 1 is a schematic fluid diagram of the calibration cell and method of the present invention;

FIG. 2 is a vertical sectional view of the calibration cell of FIG. 1 and;

FIG. 3 is a planar sectional view along the lines 3—3 of FIG. 2.

In FIG. 1, a sample solution containing an ion whose concentration is to be measured is admitted from a fluid inlet line 10 to a calibration cell 12 via a valve 14, a filter 16, a pressure regulator 18, a flow meter 20, and a pH adjustment element 22. The valve 14 is selectively operated to admit samples of the fluid to the cell 12 whenever a measurement of the ion concentration of the fluid is to be made or whenever the cell is to be calibrated. In the physical embodiment of the invention illustrated herein, the valve 14 is opened for as long as necessary to fill the cell 12 with the desired volume of liquid and is thereafter closed to block further flow during measurement or calibration.

The pH adjuster 22 establishes a desired level of pH for measurement and calibration. It is particularly useful in connection with measurements of concentration of ions such as sodium, since sodium-sensitive electrodes are particularly susceptible to additive interference from hydrogen ions, particularly a low sodium concentration levels. Fixing the pH of the solution during the measurement minimizes this interference. The pH adjustment element may be omitted, of course, in applications where hydrogen ion sensitivity is not a problem.

Referring now to FIG. 2, the measuring and calibration cell is shown in more detail. The cell comprises a housing 14 on which is mounted a well 16 having an end cap 18 closing the top thereof. A cylindrical recess in the housing 14 forms a lower cell volume 20. An upper cell volume 22, is formed by the extention of the well 16 above the housing 14. A baffle plate 24, extending laterally across the cell, divides the cell volumes into two portions, namely, lower cell volumes 20a and 20b and upper cell volumes 22a and 22b, respectively. The baffle is wider at that portion above the top face 14b of housing 14 and the lower faces of the upper side portions 24d, 24e of the baffle rest in a groove (not shown) on the face 14b. A slight clearance is provided between the lower side edges 24a of the baffle and the interior wall 14a defining the lower cell volume so as to insure that the portions 20a and 20b of the lower cell volume 20 are in free liquid communication with each other. Similiarly, a slight clearance 26b is provided between the upper portion 24b of the baffle and the interior 16b of the well 16, in order to insure that the volumes 22a and 22b of upper cell volume 22 are likewise in continuous fluid communication with each other. Additionally, a port 28 in the baffle provides further means for fluid exchange between the two portions of the cell volumes.

The liquid sample containing the ion whose concentration is to be measured is admitted to cell volumes 20 and 22 by a fluid inlet line 30 extending from the exterior of housing 14 to the interior of the lower cell volume 20. Pressurized air for "bubbling" the liquid to thereby provide good mixing between the liquid and the added standard solutions during calibration is provided from an air source (not shown) connected to conduit 31. A first drain line 32 communicates with a waster drain line 34 via a valve 36. The valve 36 has O-ring seals 38 mounted on a shaft 39. A siphon 40 has a top portion and communicates with drain 34.

When the, valve 36 is positioned to the right as shown in FIG. 2, communication between drain line 32 and drain 34 is precluded and the fluid entering the cell 12 continues to fill the interior of well 16 until it rises above the top portion of 40a of siphon 40. When this occurs, the fluid starts to flow through the siphon 40 and down to drain 34 for disposal outside the housing 14. Drainage ceases on reaching level 44 at the entrance to siphon 40 when the valve is positioned to the left, in contrast, drain line 32 communicates with drain 34 and fluid fills the cell 12 only up to a level 42 slightly above the entrance of drain line 32. Accordingly, valve 36 defines two different effective cell volumes the first corresponding to the level 42 and the second to the level 44. The former is used when monitoring the concentration of ions in the sample; the latter is used for calibration, as described more fully below. Further, the lower cell volume forms part of the upper cell volume so that both the monitoring and the calibrating measurements take place in the same physical cell although at different volumes.

A reference electrode 50 extends through the cap 18 and down into the lower cell volume 20 on one side of the baffle 24. Similarly, a measuring electrode 52 extends through the cap 18 and into the lower cell volume 20 on the other side of the baffle 24. A temperature measuring probe 54 also extends through the cap 18 adjacent to the electrode 52. Port 56, covered by a slideable cap 58, extends through the cap 18 to provide access to the interior for addition of the reagent.

The cell 12 is operated in the monitor mode by sliding valve 36 to the left to thereby insure communication between drainline 32 and drain 34. Valve 14 (FIG. 1) is then opened for a period of time sufficient to fill lower volume 20 to the point where fluid begins draining through line 32 to drain 34. At that time, valve 14 is closed. After the system has had a suitable time to stabilize, the potential generated by the reference cell-measuring cell pair 50, 52 may be recorded. The temperature, which is measured by the temperature probe 54, is also measured at this time. The measured temperature and potential, together with the predetermined reference potential and slope parameters, then are used to determine the concentration of the ions in solution.

In the calibration mode, the valve 36 is moved to the right so as to block fluid communication between drainline 32 and drain 34. Valve 14 is then opened to admit sample solution to the cell 12. The solution continues to fill the interior of the cell until it rises to the top, 40a of the syphon 40, and begins to drain downwardly through the syphon to drain 34. At this time, the valve 14 is closed and syphon 40 continues to drain fluid from the interior of the cell until the liquid level in the cell reaches the level of the mouth 40b of the syphon, at which time drainage ceases. This defines a precise liquid volume in the cell for calibration purposes. To begin the calibration, the potential generated by the electrode pair 50, 52, as well as the output of the temperature indicator 54, is measured, as was previously the case. Next, an aliquot of a concentrated solution of the ion whose concentration in the sample solution is to be determined is added via port 56. The electrode potential and temperature readings are again taken and recorded. Finally, a second aliquot of precisely defined concentration, different from the first aliquot, is added via port 56 and to the electrode and temperature measurements are again taken and recorded. The three sets of measurements are sufficient to solve with the three unknowns (reference potential, slope, and concentration) in the measurement and thereby provide the desired two calibration parameters (reference potential and slope). In an industrial device constructed for measurement of trace levels of sodium ions in the effluent from cation exchange units in a demineralization system, specifically, sodium ions, sodium levels of from 10 to 1000 ppb (parts per billion) were readily monitored to industrial accuracy. Reagent additions of 100 ppb and 1000 ppb, respectively, were used for the first and second additions.

We claim:
1. An ion-measuring instrument comprising:
   A. a calibration cell for containing a solution whose ion concentration is to be measured, the calibration cell including means within said cell defining a first, monitor-mode volume and a second, calibration-mode volume;
   B. means for measuring the ion concentration in solutions contained in the first and second volumes; and
   C. volume-control means having first and second states for draining from the calibration cell all liquid outside the first volume where the volume-control means is in its first state and for draining from the calibration cell all liquid outside the second volume when the volume-control means is in its second state, whereby the measuring means can measure the ion concentration in the first monitor-mode volume when the volume-control means is in its first state and can measure the ion concentration in the calibration-mode volume when the volume-control means is in its second state.

2. An ion-measuring instrument according to claim 1 in which said second volume is larger than, and includes, said first volume.

3. An ion-measuring instrument according to claim 1 wherein:
   A. the first volume consists of the volume in the cell below a first predetermined level and the second volume consists of the volume in the cell below a second predetermined level; and
   B. the volume-control means includes:
      i. first drain means for permitting any solution contained in the cell above the first predetermined level therein to drain from the cell;
      ii. second drain means for permitting any solution contained in the cell above the second predetermined level to drain from the cell; and
      iii. flow-control means having first and second states and interposed in the first drain means for preventing drainage through the first drain means when the flow-control means is in its second state and for permitting drainage through the first drain means when the flow-control means is in its first state.

4. An ion-measuring instrument according to claim 3 including a baffle in said volumes and means on a first side of said baffle for agitating fluids within said volumes, wherein the means for measuring ion concentration includes a measuring electrode on said first side and a reference electrode on a second, opposite side of said baffle.

5. An ion-measuring instrument according to claim 1 wherein the means for measuring ion concentration includes a measuring electrode and a reference electrode disposed in said first and second volumes.

6. An ion-measuring instrument according to claim 5 in which said second volume is larger than, and includes, said first volume.

7. An ion-measuring instrument according to claim 6 wherein:
   A. the first volume consists of the volume in the cell below a first predetermined level and the second volume consists of the volume in the cell below a second predetermined level; and
   B. the volume-control means includes:
      i. first drain means for permitting any solution contained in the cell above the first predetermined level therein to drain from the cell;
      ii. second drain means for permitting any solution contained in the cell above the second predetermined level to drain from the cell; and
      iii. flow-control means having first and second states and interposed in the first drain means for preventing drainage through the first drain means when the flow-control means is in its second state and for permitting drainage through the first drain means when the flow-control means is in its first state.

8. An ion-measuring instrument according to claim 5 further including:
   A. a baffle in said volumes;
   B. means on a first side of said baffle for agitating fluids within said volumes;
   C. means mounting the measuring electrode on said first side; and
   D. means mounting a reference electrode on a second, opposite side of said baffle.

* * * * *